(12) United States Patent
Bansal et al.

(10) Patent No.: US 8,052,931 B2
(45) Date of Patent: Nov. 8, 2011

(54) ULTRA LOW-POWER CMOS BASED BIO-SENSOR CIRCUIT

(75) Inventors: Aditya Bansal, Yorktown Heights, NY (US); Sufi Zafar, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/651,504

(22) Filed: Jan. 4, 2010

(65) Prior Publication Data

US 2011/0163812 A1  Jul. 7, 2011

(51) Int. Cl.
*G01N 15/06* (2006.01)
*G01N 33/00* (2006.01)

(52) U.S. Cl. ...... 422/82.01; 257/2; 422/68.1; 422/82.02

(58) Field of Classification Search ............ 257/20; 422/68.1, 82.01, 82.02
See application file for complete search history.

(56) References Cited

U.S. PATENT DOCUMENTS

| | | | |
|---|---|---|---|
| 3,562,553 A * | 2/1971 | Roth ............... | 327/356 |
| 4,238,757 A | 12/1980 | Schenck | |
| 4,657,658 A | 4/1987 | Sibald | |
| 4,984,045 A | 1/1991 | Matsunaga | |
| 5,160,597 A | 11/1992 | Colapicchioni et al. | |
| 6,258,606 B1 | 7/2001 | Kovacs | |
| 6,682,936 B2 | 1/2004 | Kovacs | |
| 7,019,305 B2 | 3/2006 | Eversmann et al. | |
| 7,150,997 B2 | 12/2006 | Kovacs | |
| 7,151,301 B2 | 12/2006 | Yoo et al. | |
| 7,291,496 B2 | 11/2007 | Holm-Kennedy | |
| 7,317,216 B2 | 1/2008 | Holm-Kennedy | |
| 7,357,018 B2 | 4/2008 | Curry et al. | |
| 7,507,675 B2 | 3/2009 | Zuilhof et al. | |
| 2004/0109075 A1 | 6/2004 | Tsunai | |
| 2004/0256655 A1 | 12/2004 | Kan et al. | |
| 2005/0068015 A1 | 3/2005 | Hazucha et al. | |
| 2006/0145194 A1 | 7/2006 | Barron et al. | |
| 2006/0272942 A1 | 12/2006 | Sirringhaus | |
| 2007/0159216 A1 | 7/2007 | Lee et al. | |
| 2007/0252176 A1 | 11/2007 | Shim et al. | |
| 2008/0035494 A1 | 2/2008 | Gomez et al. | |
| 2008/0315861 A1 | 12/2008 | Chung et al. | |
| 2009/0127589 A1 | 5/2009 | Rothberg et al. | |

FOREIGN PATENT DOCUMENTS

DE  10254158 A1  6/2004
WO  2008068719 A1  6/2008

OTHER PUBLICATIONS

F. Patolsky et al., Electrical detection of single viruses, PNAS, Sep. 28, 2004, pp. 14017-14022, vol. 101, No. 39, PNAS.
H. Im et al., A dielectric-modulated field-effect transistor for biosensing, Nature Nanotechnology, Jul. 2007, pp. 430-434, vol. 2, Nature Publishing Group.

(Continued)

*Primary Examiner* — Brian J Sines
(74) *Attorney, Agent, or Firm* — Cantor Colburn LLP; Preston Young

(57) ABSTRACT

An apparatus configured to identify a material having an electric charge, the apparatus having: an inverting gain amplifier including a first field-effect transistor (FET) coupled to a second FET; wherein a gate of the first FET is configured to sense the electric charge and an output of the amplifier provides a measurement of the electric charge to identify the material.

15 Claims, 7 Drawing Sheets

OTHER PUBLICATIONS

Huang, et al. "Development of Active Matrix Biosensor Array for Cell Screening". Proc. of IEEE Sensors 2004.

K. Nakazato, et al. "CMOS Cascode Source-Drain Follower for Monolithically Integrated Biosensor Array". IEICE Trans. Electron., vol. E91-C, No. 9 Sep. 2008. pp. 1505-1515.

Han, Label-free detection of biomlecules by a field-effect transistor microarray biosensor with bio-functionalized gate surfaces, Dec. 2006 [retrieved on Mar. 17, 2011]. Retrieved from the internet:,URL: http://juwel.fz-juelich.de:8080/dspace/bitstream/2128/2597/1/Juel_4227_Han.pdf.

Notification of Transmittal of the International Search Report and the Written Opinion of the International Searching Authority, or the Declaration; PCT/US11/20007;Apr. 6, 2011.

Lee, et al., Ion-Sensitive Field-Effect Transistor for Biological Sensing, Sensors 2003, 9, 7111-7131; doi:10.3390/s90907111 [online], Sep. 7, 2009 [retrieved on Mar. 17, 2011]. Retrieved from the Internet:, URL:http://www.mdpi.com/1424-8220/9/7111/pdf.

Maher, Electrical Engineering 234 Electrical Engineering Circuit Laboratory, Manual [online], Jun. 1992 [retrieved on Mar. 17, 2011]. Retrieved from the Internet:,URL:http://www.coe.montana.edu/ee/rmaher/teaching/EEngr_234_Labs_maher.pdf>p. 8-1 to 8-20.

* cited by examiner

ULTRA LOW-POWER CMOS BASED BIO-SENSOR CIRCUIT

BACKGROUND

The present invention generally relates to sensing a biological molecule and, more particularly, to electronic circuits that automate the detection of the biological molecule using field effect transistor based sensors.

Biological molecules, which may include proteins or viruses, play an important role in many illnesses. Thus, the identification of biological molecules or biomolecules is essential for improved and cost effective disease diagnosis and treatment.

Conventional techniques used to detect the biomolecules include fluorescence or radioactive labeling, and patch clamp. Unfortunately, these conventional techniques can be labor intensive and costly, thereby, reducing the number of patients who may have been helped if these techniques were more cost effective.

Therefore, there is a need for improved techniques for detecting biomolecules. More particularly, the improved techniques need to be less labor intensive and less costly than the conventional techniques.

SUMMARY

The shortcomings of the prior art are overcome and additional advantages are provided through the provision of an apparatus configured to identify a material having an electric charge, the apparatus having: an inverting gain amplifier including a first field-effect transistor (FET) coupled to a second FET; wherein a gate of the first FET is configured to sense the electric charge and an output of the amplifier provides a measurement of the electric charge to identify the material.

Also disclosed is a method for identifying a material having an electric charge, the method including: sensing the electric charge with a gate of a first field effect transistor (FET), the first FET and a second FET forming an inverting gain amplifier circuit having an output that provides a measurement of the electric charge; and measuring the electric charge with the inverting gain amplifier circuit to identify the material.

Further disclosed is a non-transitory machine-readable medium including machine-executable instructions for identifying a material having an electric charge by implementing a method including: sensing the electric charge with a gate of a first field effect transistor (FET), the first FET and a second FET forming an inverting gain amplifier circuit having an output that provides a measurement of the electric charge; measuring the electric charge with the inverting gain amplifier circuit to identify the material; and at least one of storing the measurement, analyzing the measurement, and presenting the measurement to a user.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other objects, features, and advantages of the invention are apparent from the following detailed description taken in conjunction with the accompanying drawings, wherein like elements are numbered alike, in which:

DETAILED DESCRIPTION

Disclosed are improved techniques for sensing or detecting a biomolecule, the terms sensing and detecting being used interchangeably herein. The techniques, which include apparatus and method, call for using a field effect transistor (FET) as a sensor for sensing the biomolecule. The techniques provide embodiments of circuits that automate the detection and, thus, identification of the biomolecule using the FET sensor. In addition, the techniques call for fabricating an automated sensing platform using standard complementary metal-oxide-semiconductor (CMOS) technology. Thus, the automated detection and the standard fabrication technology provide for biomolecule detection that is efficient and cost effective.

An array of sensor cells is used to detect the biomolecule where each sensor cell includes at least one FET sensor and associated circuitry for amplifying a signal from the FET sensor. The signal, such as a voltage reading, is used to detect the biomolecule. In addition, circuitry may be provided to select a reading (i.e., signal) from a particular sensor cell and for conserving power.

There are at least two advantages to using an array of sensor cells. One is that one sensor reading may be used to confirm or validate a reading from another sensor cell. Another is that certain sensor cells may have FET sensors optimized for detecting a particular type of biomolecule.

Figure 1:
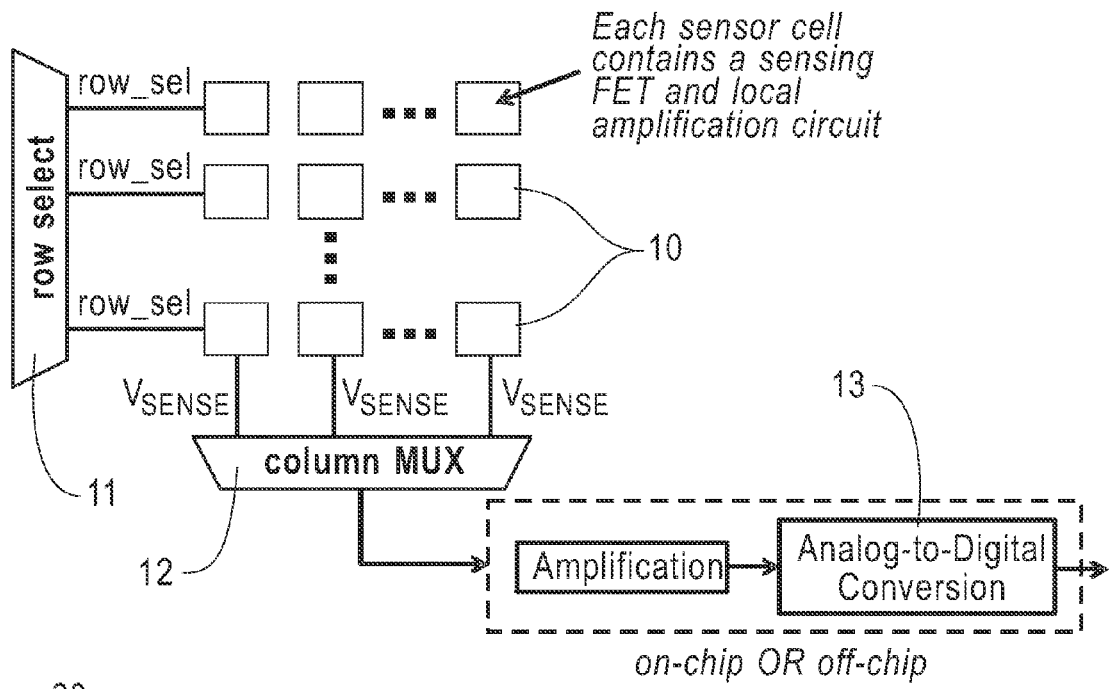
FIG. 1 illustrates an exemplary embodiment of an array of sensor cells.

Reference may now be had to FIG. 1. FIG. 1 illustrates an exemplary embodiment of an array of sensor cells 10. Each sensor cell 10 is configured to sense a biomolecule and provide a signal such as a voltage reading that can be used to detect the biomolecule. The array of sensor cells 10 in the embodiment of FIG. 1 is a matrix arrangement wherein each cell 10 is defined by a row number and a column number. In the embodiment of FIG. 1, a row select circuit 11 is configured to select a row of cells 10 to be read by energizing each sensor cell 10 in the selected row. A column multiplexing circuit 12 is configured to read a signal from one cell 10 in each column. Thus, by selecting a row, each cell 10 within the row will be read by the column multiplexing circuit 12.

Still referring to FIG. 1, the amplified signal or voltage reading for each cell 10 is referred to as $V_{SENSE}$. $V_{SENSE}$ is sent to relatively long interconnect lines to be transferred outside of the array for further processing. $V_{SENSE}$ may be amplified again outside of the sensor cell 10 and then converted to a digital signal via an analog to digital converter (ADC) 13. In one embodiment, there can be as many ADCs as there are sensor cells 10 in a row, so that all $V_{SENSE}$ outputs from each row can be simultaneously converted to the digital signal. In another embodiment, there can be less ADCs. Using less ADCs requires selecting the $V_{SENSE}$ signals in an order using the column multiplexing circuit. This will take more time to perform the analog to digital conversion, but an advantage is that less area will be required on a semiconductor chip.

Figure 2:
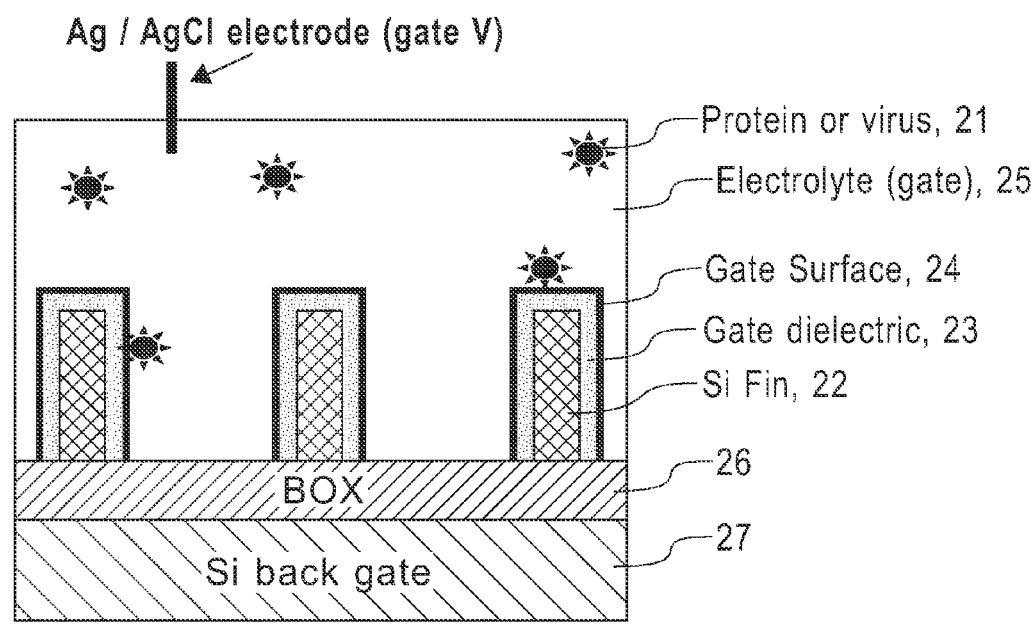
FIG. 2 illustrates an exemplary embodiment of a field effect transistor (FET) configured to sense a biomolecule.

Reference may now be had to FIG. 2. FIG. 2 illustrates an exemplary embodiment of an FET 20 configured to sense a biomolecule 21. The FET 20 in the embodiment of FIG. 1 is a finFET having a fin 22 covered with a gate dielectric 23. One non-limiting embodiment of the gate dielectric 23 is $SiO_2$/$HfO_2$. The gate dielectric 23 is covered with a gate surface material 24 that is configured to adhere to the biomolecule 21. The FET 20 does not have a conventional top gate. An electrolyte 25 surrounds the gate surface material 24 and acts as the top gate. The fin 22 and the gate dielectric 23 are situated atop a buried oxide (BOX) layer 26 that is situated atop of a silicon layer 27, which is the back gate of the FET 20.

The drain current of the FET 20 is operated in the sub-threshold region. To sense the biomolecule 21, the biomolecule 21 binds to the gate surface material 24 and transfers an electric charge to the gate dielectric 23. The electric charge at the gate dielectric 23 affects the drain current, which in turn affects the drain to source voltage of the FET 20. The measured drain to source voltage is $V_{SENSE}$. In that each different biomolecule 21 generally has a unique electrical charge, the measurement of $V_{SENSE}$ can be used to identify the specific biomolecule 21 being detected.

The advantage of using an FET 20 to sense the biomolecule 21 is that the FET 20 has high sensitivity to the electric charge of the biomolecule 21. The high sensitivity results from a small sub-threshold slope such that a small change in the gate voltage causes a large change in the drain current resulting in a large change in the drain to source voltage (i.e., $V_{SENSE}$). The larger surface area of the gate dielectric 23 in finFETs compared to non-fin FETs results in an improved response time. The finFET used as the FET 20 can have a single fin or an array of fins to further increase the surface area of the gate dielectric 23.

While the embodiment of FIG. 2 illustrates a finFET, other types of FETs may also be used to detect the biomolecule 21. The FET 20 is generally implemented using complementary metal-oxide-semiconductor (CMOS) technology.

Figure 3:
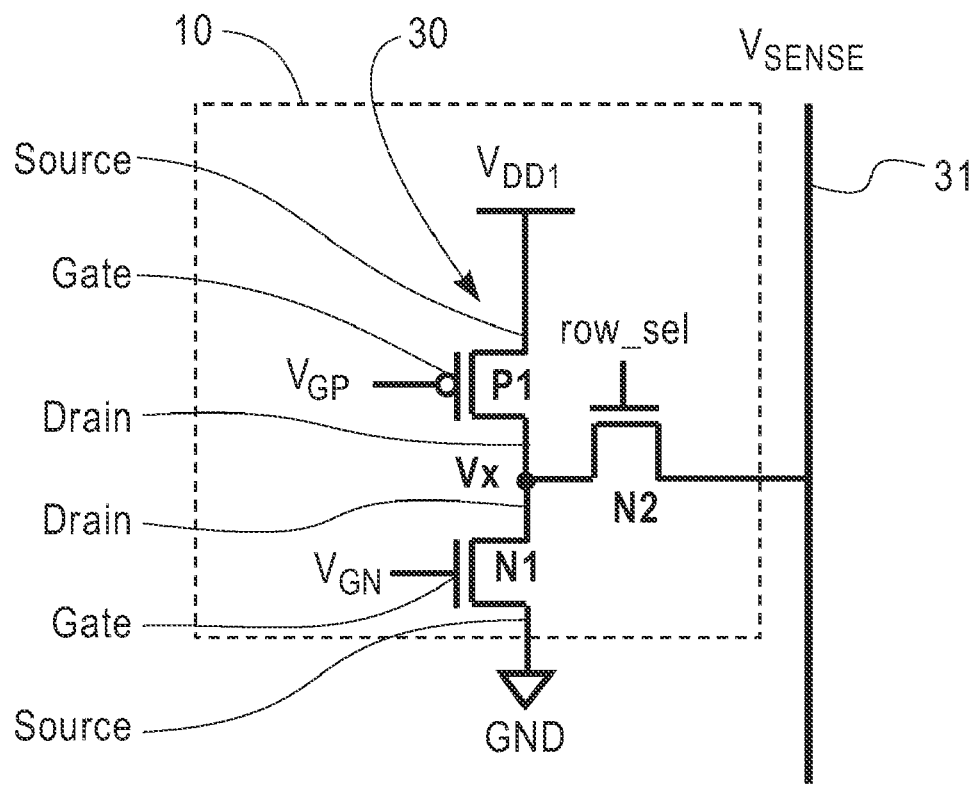
FIG. 3 illustrates a schematic diagram of an inverting gain amplifier circuit that includes the sensor FET.

Reference may now be had to FIG. 3. FIG. 3 illustrates a schematic diagram of an inverting gain amplifier circuit 30. The inverting gain amplifier circuit 30 includes the FET 20 as the sensor for sensing the biomolecule 21. In the embodiment of FIG. 3, the FET 20 is an n-type FET and is designated FET N1. The FET N1 is coupled in series with a p-type FET, FET P1. That is, the drain of FET N1 is coupled to the drain of FET P1 and the source of FET P1 is coupled to a power supply designated $V_{DD1}$ and supplying voltage $V_{DD1}$. Together, the FET N1 and the FET P1 form the inverting gain amplifier circuit 30. In addition, another n-type FET, FET N2, transfers the output of the FET N1, $V_X$, which is related to the detected electric charge of the biomolecule 21, to a $V_{SENSE}$ line 31. The voltage read at the $V_{SENSE}$ line 31 is referred to as $V_{SENSE}$. In the embodiment of FIG. 3, the $V_{SENSE}$ line 31 is outside of the sensor cell 10. The FET N2 is configured to receive a "row select" signal (i.e., row_sel) from the row select circuit 11 such that when a gate of the FET N2 is energized (i.e., set to $V_{DD1}$), then the output voltage, $V_X$, is coupled to the $V_{SENSE}$ line 31. When FET N2 is "ON", then $V_{SENSE}$ becomes generally the same as $V_X$.

Figure 4:
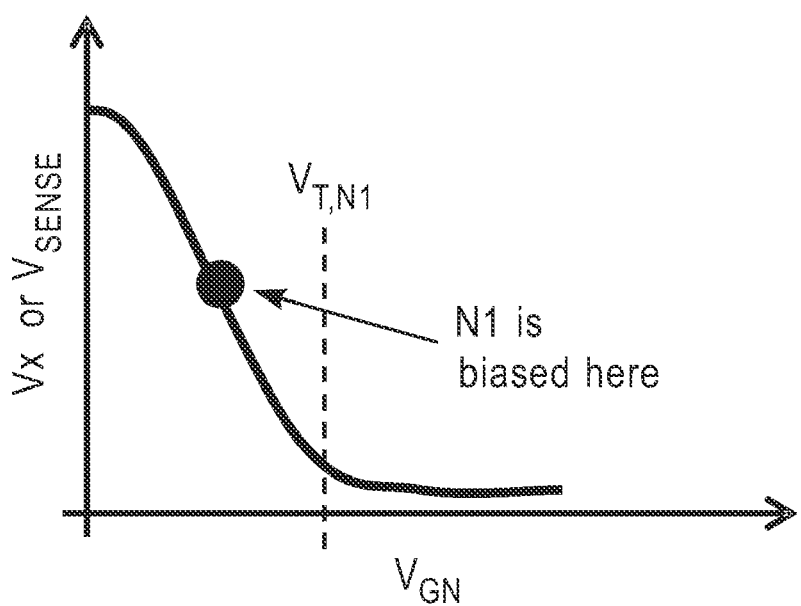
FIG. 4 depicts aspects of inverting gain characteristics of the inverting gain amplifier circuit.

Reference may now be had to FIG. 4. FIG. 4 depicts aspects of inverting gain characteristics of the inverting gain amplifier circuit 30. The output of the amplifier circuit 30 is graphed versus the gate voltage, $V_{GN}$, of FET N1. The sensing FET N1 is biased to operate in the sub-threshold region, such that $0 < V_{GN} < V_{T,N1}$. The p-type FET P1 is biased to operate such that $V_{GP} \leq V_{DD1} - V_{T,P1}$, where $V_{T,P1}$ is the threshold of the p-type FET P1. If the gate voltage, $V_{GN}$, of FET N1 increases, then the voltage, $V_X$, will decrease according to the slope of the operating region in the curve in FIG. 4. Similarly, if the gate voltage, $V_{GN}$, of FET N1 decreases, then the voltage, $V_X$, increases according to the slope of the operating region in that curve. Because of the high sensitivity of the FET N1, a small change in $V_{GN}$ will generally result in a large change in $V_X$.

Figure 5:
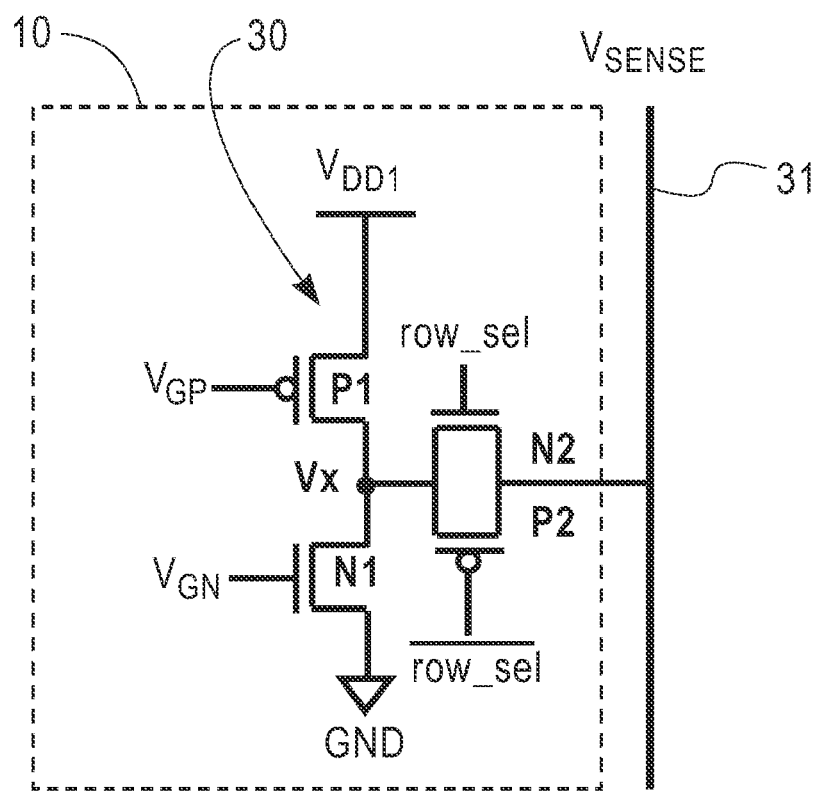
FIG. 5 depicts aspects of one sensor cell having a circuit configured to have low resistance in the components coupling output of the inverting gain amplifier circuit to a sensing line.

Reference may now be had to FIG. 5. FIG. 5 depicts aspects of the sensor cell 10 having a circuit configured to have low resistance in the components coupling $V_X$ to the $V_{SENSE}$ line. In the circuit of FIG. 5, a p-type FET, FET N2, is disposed in parallel to FET N2 such that the gate of FET N2 is coupled to the complement of the row select signal. This configuration will transfer a wide range of values of $V_X$ to the $V_{SENSE}$ line. However, it is noted that this configuration will also increase leakage in the sensor cells 10 that are not selected for reading.

In the unselected sensor cells 10, there is a current path between $V_{DD1}$ and ground, GND. This can result in power consumption by a sensor cell 10 even if the cell 10 is not accessed for reading. Three examples of techniques to overcome this power consumption are disclosed herein as described with reference to FIGS. 6, 7 and 8.

Figure 6:
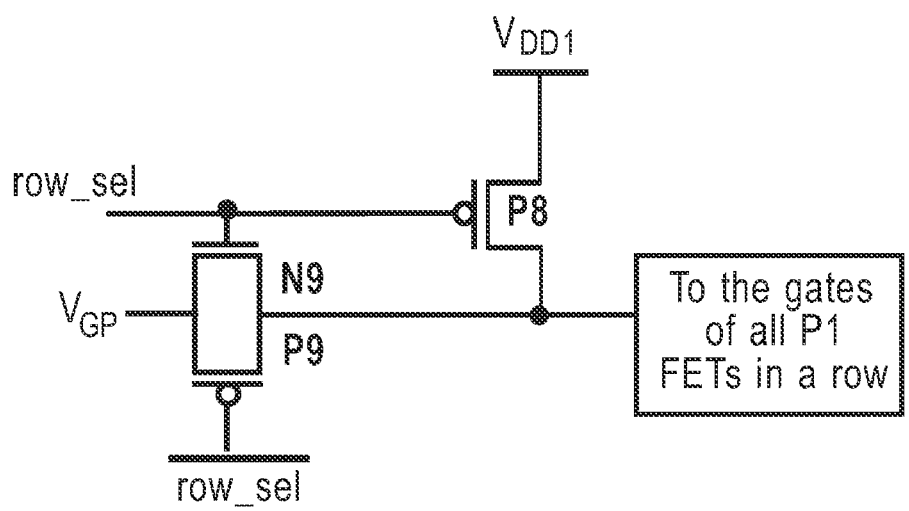
FIG. 6 depicts aspects of a circuit configured to turn off an FET in sensor cells 10 that are not selected for obtaining a measurement.

Reference may now be had to FIG. 6. FIG. 6 depicts aspects of a circuit configured to turn off the FET P1 in the sensor cells 10 that are not selected for reading. The circuit in FIG. 3 includes a p-type FET, FET P8, disposed between $V_{DD1}$ and gates of all P1 FETs in a row of the array. Further, n-type FET N9 and p-type FET P9 are connected in parallel such that their drains are tied together and connected to $V_{GP}$ and their sources are connected to the gate of all P1 FETs in the row of the array. The gates of FET P8 and FET N9 are connected to the row enable signal "row_sel." The gate of FET P9 is connected to the complement of the "row_sel" signal. This circuit is common to all sensor cells 10 in a row. All the sensor cells 10 in a row have a common $V_{GP}$. In the sensor cells 10 that are unselected, the row select will be "0" and, hence, the FET P8 will be ON connecting gates of all P1 FETs in a row to $V_{DD1}$. Thus, in all the unselected sensor cells 10, the FET P1 will be turned OFF to stop the current flowing in the path $V_{DD1}$ to GND. In a selected row, FET P8 will be OFF and FET P9 and FET N9 will be ON so as to connect the gate of all P1 FETs in the row to $V_{GP}$.

Figure 7:
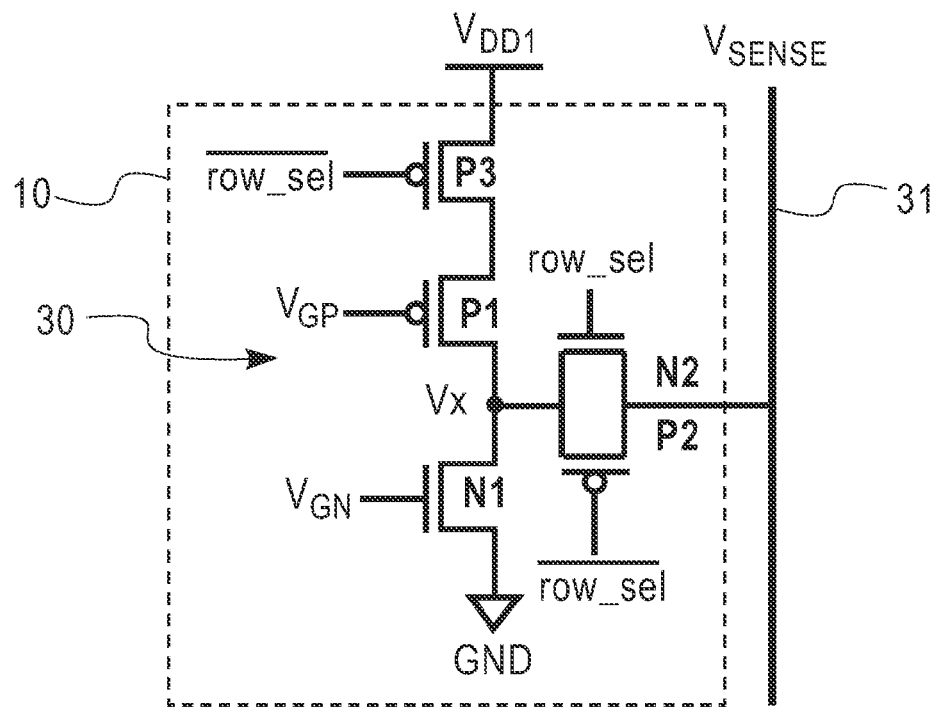
FIG. 7 depicts aspects of a circuit having a p-type FET disposed in series with a source of a p-type FET in the inverting gain amplifier circuit and configured to de-energize the inverting gain amplifier circuit.

Reference may now be had to FIG. 7. FIG. 7 depicts aspects of a circuit having a p-type FET, FET P3, disposed in series with the FET P1, i.e., between the power supply $V_{DD1}$ and the source of the FET P1. The FET P3 is turned OFF when a row is not selected, i.e., when the row select signal is low, thus, stopping the current flowing in the path $V_{DD1}$ to GND.

Figure 8:
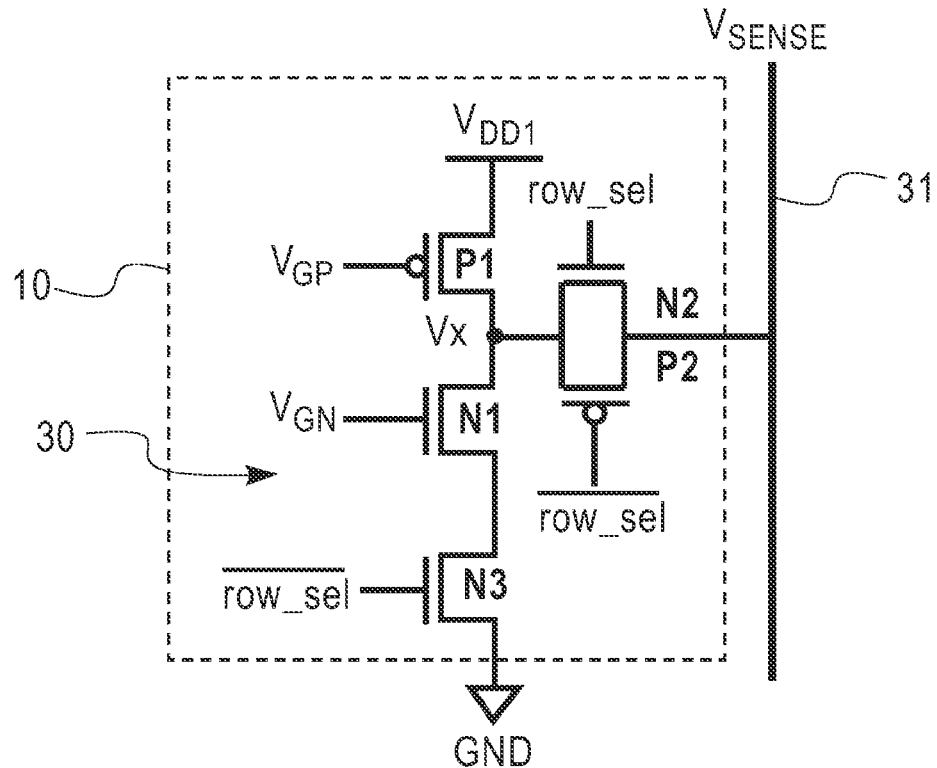
FIG. 8 depicts aspects of a circuit having an n-type FET disposed in series with a source of the sensor FET in the inverting gain amplifier circuit and configured to de-energize the inverting gain amplifier circuit.

Reference may now be had to FIG. 8. FIG. 8 depicts aspects of a circuit having an n-type FET, FET N3, disposed in series with the FET N1, i.e., between the source of the FET N1 and the ground, GND. The FET N3 is turned OFF when a row is not selected, i.e., when the row select signal is low, thus, stopping the current flowing in the path $V_{DD1}$ to GND.

With reference to FIG. 1, several sensor cells 10 may be connected to the common $V_{SENSE}$ line resulting in the $V_{SENSE}$ line being very long and, hence, having a relatively large resistance and capacitance. At any given time, only one selected sensor cell 10 may have a measurement transmitted to the $V_{SENSE}$ line while the FET N2 (shown in FIGS. 3, 5, 7 and 8) in other unselected sensor cells 10 is OFF. Since the FET N1 and the FET P1 are operating in the sub-threshold region and not in deep saturation (which occurs when $V_{GN}=V_{DD1}$ and $V_{GP}=0$), the electrical currents through the FET N1 and the FET P1 are very low. Hence, charging and/or discharging of a connection line connecting the $V_X$ signal to the $V_{SENSE}$ line through the FET N1 and the FET P1 can contribute significant noise to the $V_X$ signal. In addition, the charging and/or discharging can cause an increase in the amount of time it takes to stabilize the $V_X$ signal transmitted to the $V_{SENSE}$ line. In order to prevent the noise and decrease the stabilization time, an amplifying and decoupling circuit disposed in the connection line is disclosed.

Figure 9:
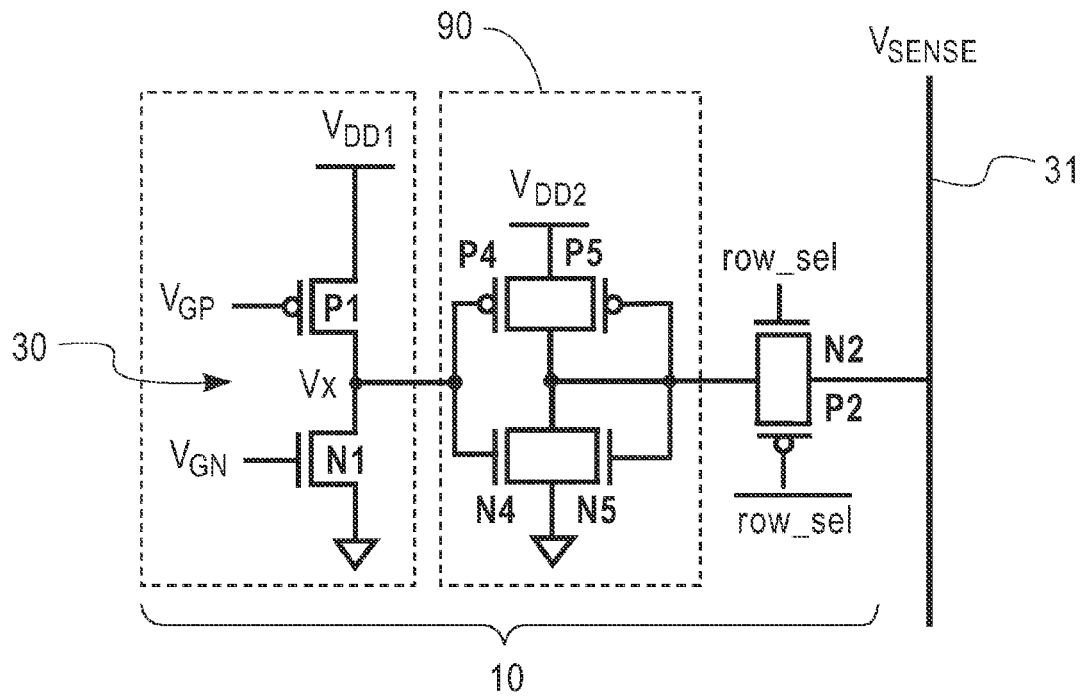
FIG. 9 depicts aspects of an amplifying and decoupling circuit configured to decouple and amplify a measurement signal from the $V_{SENSE}$ line and also linearly amplifies the $V_X$ signal in the range of $\Delta V_{GN}$ before the $V_X$ signal is transmitted to the $V_{SENSE}$ line.

Reference may now be had to FIG. 9. FIG. 9 depicts aspects of an amplifying and decoupling circuit 90 that decouples the $V_X$ signal from the $V_{SENSE}$ line and also linearly amplifies the $V_X$ signal in the range of $\Delta V_{GN}$ before the $V_X$ signal is transmitted to the $V_{SENSE}$ line. The amplifying and decoupling circuit 90 includes n-type FETs, FET N4 and FET N5, and p-type FETs, FET P4 and FET P5. FETs N4, N5, P4 and P5 are configured as shown in FIG. 9 between (1) a node at the inverting gain amplifier circuit 30 providing the $V_X$ signal and (2) the $V_{SENSE}$ line. It is noted that FET N4 and FET P4 are in an inverter configuration with the $V_X$ signal as input and $V_{SENSE}$ as output. FET N5 and FET P5 are feedback transistors. In another embodiment, multiple gate FETs such as finFETS with independent backgate control may be used in lieu of the single gate FETs to make the amplifying and decoupling circuit 90. FET N4 and FET N5 can be substituted with a single multiple gate FET with FET N5 as a backgate. Similarly, FET P4 and FET P5 can be substituted with a single multiple gate FET with FET P5 as a backgate. As shown in FIG. 9, the amplifying and decoupling circuit 90 is coupled to a separate power supply $V_{DD2}$ (having voltage $V_{DD2}$) so as to achieve a desired voltage range for $V_{SENSE}$.

The inverting gain amplifier circuit 30 is based on the change in $V_X$ due to a change in $V_{GN}$. The change in $V_X$ due to a change in $V_{GN}$ can be deterministically correlated when $\Delta V_X/\Delta V_{GN}$ is a definite function in the given range of $\Delta V_{GN}$. As FET N1 and FET P1 form an inverting gain circuit, the gain is very high near the biasing point, i.e., at the chosen value of $V_{GN}$ as shown in FIG. 4. Amplification of $V_{GN}$ is beneficial but the amplification can limit the range if values of $\Delta V_{GN}$ due to saturation of $V_X$ for low or high values of $V_{GN}$. It is preferable to have correlation between $\Delta V_X$ and $\Delta V_{GN}$ in the full range of values of $\Delta V_{GN}$.

Figure 10:
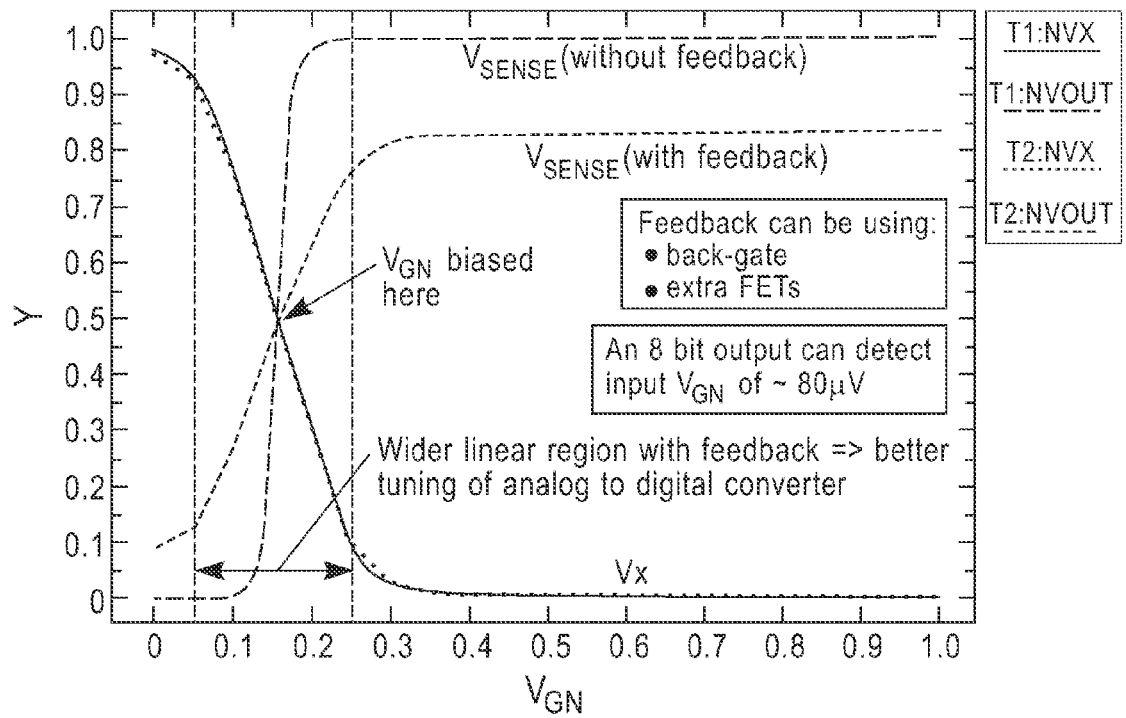
FIG. 10 illustrates plots of output of the inverting gain amplifier versus gate voltage of the sensor FET.

Reference may now be had to FIG. 10. FIG. 10 illustrates plots of $V_{SENSE}$ and $V_X$ versus $V_{GN}$. It is noted that linearization circuitry results in a linear correlation between $V_{SENSE}$ and $V_{GN}$ for a wide range of $\Delta V_{GN}$ from the biasing point. FIG. 10 also shows a plot of $V_{SENSE}$ with and without the feedback FETs N5 and P5. Without feedback, the output of the inverting gain amplifier circuit 30 has very high amplification, thereby, having the potential for a large change in $V_{SENSE}$ for a little change in $V_{GN}$. Thus, $V_{SENSE}$ can saturate for a large change in $V_{GN}$. This potential for saturation limits the region of operation of $V_{GN}$, hence, feedback is necessary for detecting the large change in $V_{GN}$, due to detecting a large change in electric charge of the biomolecule 21.

Figure 11:
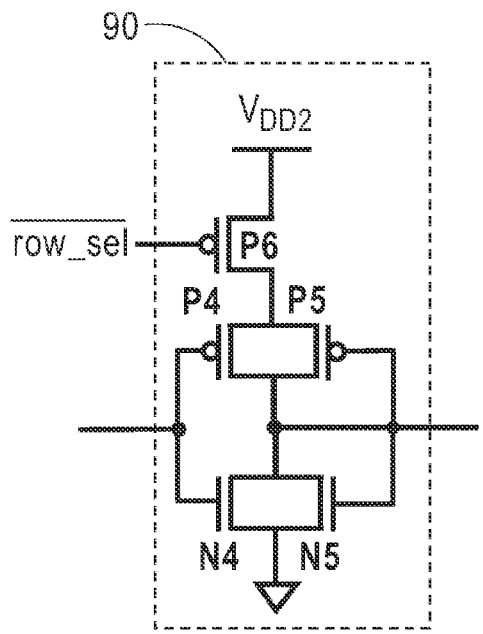
FIGS. 11 and 12 depict embodiments for interrupting a current path to the inverting gain amplifier.
Figure 12:
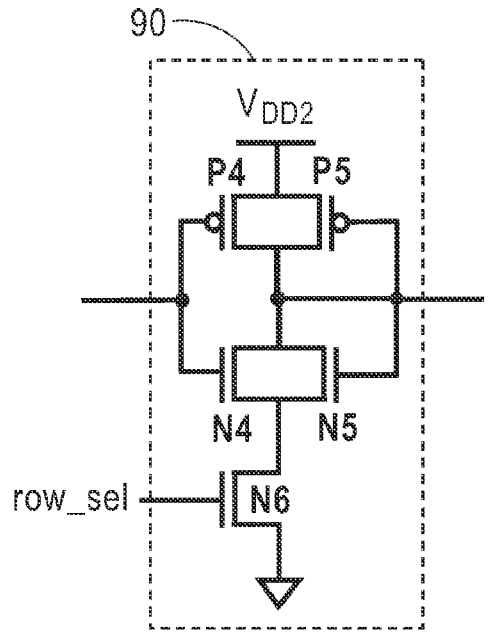

To reduce power consumption in the amplifier and decoupling circuit 90, the electric current path between power supply $V_{DD2}$ and GND as shown in FIG. 9 can be interrupted. FIG. 11 depicts an embodiment for interrupting the current path by disposing a p-type FET, FET P6, between the power supply $V_{DD2}$ and the sources of FETs P4 and P5. FIG. 12 depicts another embodiment for interrupting the current path by disposing an n-type FET, FET N6, between the sources of FETs N4 and N5 and ground.

The amplifying and decoupling circuit 90, which may include the current interrupting circuitry, can be implemented in each sensor cell 10 or, alternatively, by sharing the circuit 90 with the sensor cells 10 in a column. In the sharing embodiment, the amplifying and decoupling circuit 90 is coupled between the $V_{SENSE}$ line and the column multiplexing circuit 12 shown in FIG. 1 to reduce the area needed by each sensor cell 10.

Sensor calibration to mitigate fabrication related variations is discussed next. Due to fabrication imperfections in a semiconductor chip used to fabricate the array of sensor cells 10, FETs in the bio-sensing cell 10 may not have desired gate length, width, threshold voltage etc. Hence, pre-fabrication calibration of $V_{SENSE}$ to $\Delta V_{GN}$ may not be accurate. Therefore, post-fabrication calibration of each sensor cell 10 is disclosed. Post-fabrication can be achieved in the following way. First, select a $V_{GN}$ based on pre-fabrication analysis. Second, in the fabricated chip, apply $V_{GN}$ and measure the $V_{SENSE}$ (called $V0_{SENSE}$) for each sensor cell 10. It is noted that the biomolecule 21 is not present for this calibration measurement. $V0_{SENSE}$ is the analog voltage signal that is converted to a digital signal, which can be stored in a conventional semiconductor memory integrated onto the chip or connected externally. The stored digital value of $V0_{SENSE}$ for each sensor cell 10 will serve as reference point for future measurements performed by that sensor cell 10. Third, during a real sensing application, the measured digital value of $V_{SENSE}$ will be in reference to original stored value of $V0_{SENSE}$. This calibration technique does not require any changes in the hardware. Hence, the same hardware can be repeatedly used for different kinds of biomolecules 21 after quick calibration i.e., measurement of $V0_{SENSE}$.

Figure 13:
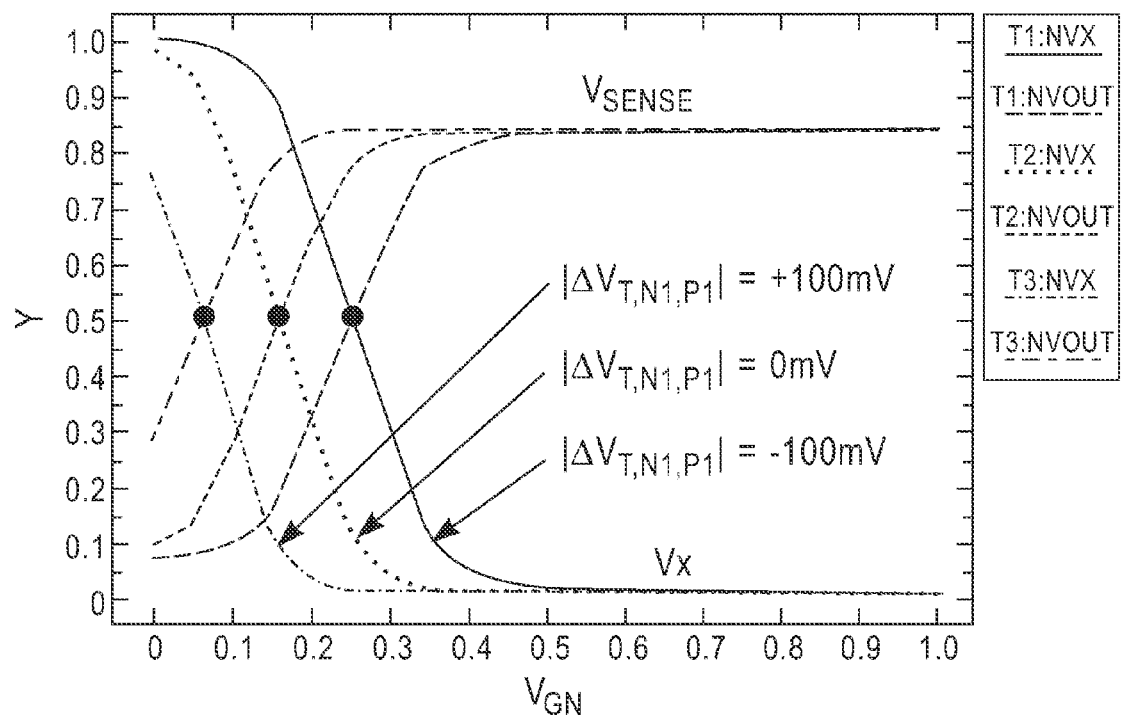
FIG. 13 illustrates movement of a biasing point of the gate voltage of the sensor FET corresponding to a change in the voltage thresholds of the sensor FET and another FET in the inverting gain amplifier circuit.

Sensor tuning to test a variety of the biomolecules 21 that may require different biasing points ($V_{GN}$) is discussed next. The range of operation of the sensing FET N1 depends on the choice of biasing point $V_{GN}$. The biological molecule 21 should not experience any resistance due to $V_{GN}$ while binding to the gate of the FET N1. If different biomolecules 21 require different biasing points, i.e., $V_{GN}$ values, then the similar $\pm\Delta V_{GN}$ values can be determined. This can be achieved by dynamically controlling the threshold voltage $V_T$ of FETs N1 and P1. FIG. 13 illustrates the movement of biasing point $V_{GN}$ with the change in $V_T$ of FETs N1 and P1. This $\Delta V_{T, N1, P1}$ can be achieved by changing the substrate bias of FETs N1 and P1 (i.e., single gate FETs) with substrate contact. In multiple-gate FETs such as finFETs, $V_T$ can be dynamically modified by controlling the voltage bias at the back (or second) gate of these FETs.

Figure 14:
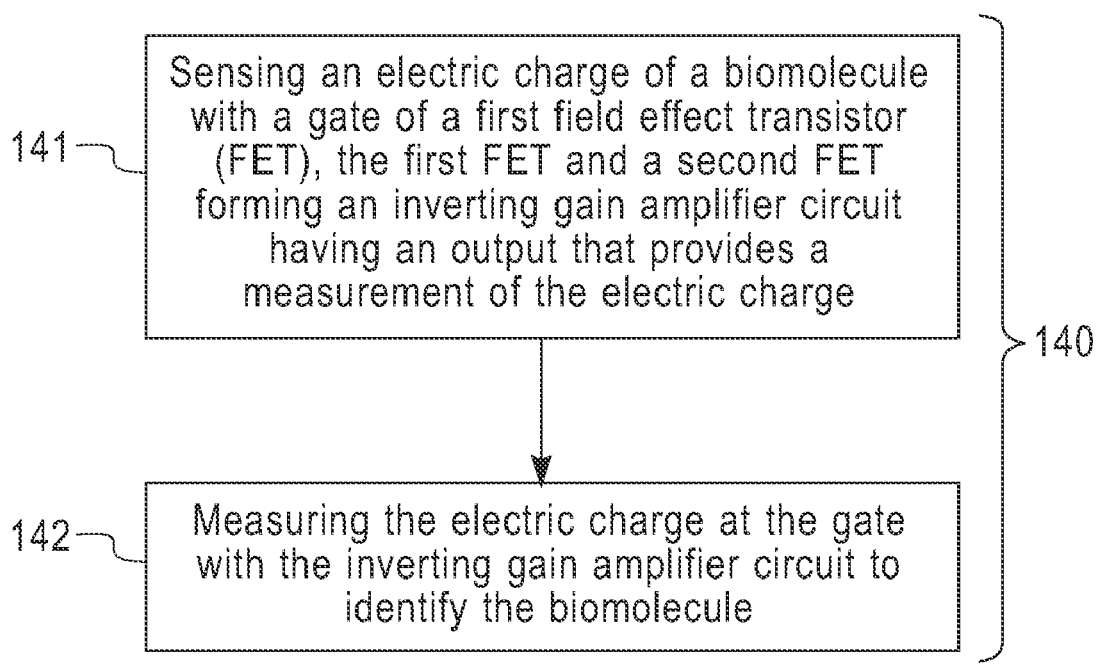
FIG. 14 presents one example of a method for identifying a biomolecule having an associated electric charge.

FIG. 14 presents one example of a method 140 for identifying the biomolecule 21 having an associated electric charge. The method 140 calls for (step 141) sensing the electric charge of the biomolecule 21 with the gate dielectric 23 of the FET 20. The FET 20 and another FET are configured to form the inverting gain amplifier circuit 30. Further, the method 140 calls for (step 142) measuring the electric charge at the gate with the inverting gain amplifier circuit to identify the biomolecule 21.

While the method 140 and the discussion presented above are with respect to identifying the biomolecule 21, any material having an electric charge that may adhere to the gate dielectric 23 can be identified. In general, testing and/or analysis of different biomolecules 21 and materials having differing electric charges are used to determine a reference electric charge associated with each test biomolecule 21/material. Thus, by comparing the measured electric charge with reference electric charges, the biomolecule 21/material can be identified.

In one embodiment, the array of sensors 10 can be built into one CMOS device or semiconductor "chip" to lower production cost and improve reliability. In addition, other components used with the array of sensors 10, such as the row select circuit 11, the column multiplexing circuit 12 and the ADC 13, can also be built into the same CMOS device.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

In support of the teachings herein, various analysis components may be used, including a digital and/or an analog system. The system may have components such as a processor, storage media, memory, input, output, communications link, user interfaces (such as a printer or a display), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second," "third," etc. are used to distinguish elements and are not used to denote a particular order. The term "couple" relates to one component being coupled either directly to another component or indirectly to the another component via one or more intermediate components.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus configured to identify a material having an electric charge, the apparatus comprising:
    an array of sensor cells, each of the sensors cells including
        a gate surface configured to cause the sensor cell to produce a signal based on the electric charge of the material, each sensor cell including an inverting gain amplifier comprising a first field-effect transistor (FET) coupled to a second FET,
    a gate of the first FET is coupled to the signal and an output of the amplifier provides an output value that identifies the material;
    a row select circuit and a column multiplexing circuit configured to obtain output value from each sensor cell in the array.

2. The apparatus of claim 1, wherein the material is a biological molecule.

3. The apparatus of claim 1, wherein the first FET is an n-type FET and the second FET is a p-type FET.

4. The apparatus of claim 3, wherein the first FET is biased below a voltage threshold of the first FET.

5. The apparatus of claim 3, wherein a drain of the first FET is coupled to a drain of the second FET at a node wherein a voltage at the node provides the output.

6. The apparatus of claim 5, wherein a source of the second FET is coupled to a first power supply.

7. The apparatus of claim 6, further comprising a third FET disposed between a gate of the second FET and the first power supply and configured to turn off the second FET.

8. The apparatus of claim 6, wherein the output is provided to a sensing line configured to receive the output.

9. The apparatus of claim 8, further comprising a third FET, n-type disposed between the node and the sensing line and having a drain coupled to the node and source coupled to the sensing line, the third FET being configured to receive a signal from a select circuit to enable sending the output to the sensing line.

10. The apparatus of claim 9, further comprising a fourth FET, p-type, disposed between the node and the sensing line and having a drain coupled to the node and source coupled to the sensing line, the fourth FET being configured to receive the signal from the select circuit to enable sending the output to the sensing line.

11. The apparatus of claim 10, further comprising an amplifying and decoupling circuit disposed between the node and the drains of the third FET and the fourth FET.

12. The apparatus of claim 11, wherein the amplifying and decoupling circuit comprises:

a fifth FET, n-type, and a sixth FET, p-type, each having a gate coupled to the first node and each having a drain coupled to a second node; and a seventh FET, n-type, and an eighth FET, p-type, each having a gate and a drain coupled to the second node;

wherein the second node is coupled to the drains of the third FET and the fourth FET.

13. The apparatus of claim 12, wherein a source of the sixth FET and a source of the eighth FET are coupled to a second power supply.

14. The apparatus of claim 1, wherein the array of sensor cells is built into one CMOS device.

15. The apparatus of claim 1, wherein the first FET is a selection from a group consisting of a finFET and a metal oxide semiconductor (MOSFET).

* * * * *